(12) United States Patent
Chung et al.

(10) Patent No.: US 8,492,438 B2
(45) Date of Patent: *Jul. 23, 2013

(54) TREATMENT SKIN DISORDERS

(75) Inventors: Yih-Lin Chung, Taipei (TW); Nam-Mew Pui, Taipei (TW); Wei-Wei Chang, Boston, MA (US)

(73) Assignee: Asan Laboratories Company (Cayman), Limited, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/021,063

(22) Filed: Feb. 4, 2011

(65) Prior Publication Data

US 2011/0212161 A1   Sep. 1, 2011

Related U.S. Application Data

(63) Continuation-in-part of application No. 12/700,843, filed on Feb. 5, 2010, now Pat. No. 8,163,764, which is a continuation-in-part of application No. 11/848,272, filed on Aug. 31, 2007, which is a continuation-in-part of application No. 11/499,936, filed on Aug. 7, 2006, which is a continuation-in-part of application No. 10/798,119, filed on Mar. 11, 2004, which is a continuation-in-part of application No. 10/205,738, filed on Jul. 25, 2002, now Pat. No. 6,809,118, said application No. 11/848,272 is a continuation-in-part of application No. 10/843,025, filed on May 10, 2004, which is a continuation-in-part of application No. 10/205,738, filed on Jul. 25, 2002, now Pat. No. 6,809,118, said application No. 11/848,272 is a continuation-in-part of application No. 11/079,370, filed on Mar. 14, 2005, which is a continuation-in-part of application No. 10/132,999, filed on Apr. 26, 2002, now abandoned.

(51) Int. Cl.
*A61K 31/19* (2006.01)

(52) U.S. Cl.
USPC ............ 514/570; 514/575; 514/557; 514/559

(58) Field of Classification Search
USPC .................. 514/570, 575, 557, 559
See application file for complete search history.

(56) References Cited

U.S. PATENT DOCUMENTS

| | | | |
|---|---|---|---|
| 6,809,118 B2 * | 10/2004 | Chung | 514/570 |
| 2009/0186809 A1 * | 7/2009 | Hentsch et al. | 514/9 |

* cited by examiner

*Primary Examiner* — Rei-tsang Shiao
(74) *Attorney, Agent, or Firm* — Occhiuti Rohlicek & Tsao LLP

(57) ABSTRACT

Disclosed are a composition and a method for treating skin disorders, including rosacea, pityriasis rosea, erythema, rhinophyma, and rosacea-associated disorders including pimples, papules, pustules, and telangiectasia.

19 Claims, 2 Drawing Sheets

TREATMENT SKIN DISORDERS

CROSS REFERENCE TO RELATED APPLICATIONS

This application claims the priority of U.S. Application 61/301,655, filed on Feb. 5, 2010 and is a continuation-in-part of U.S. application Ser. No. 12/700,843, filed on Feb. 5, 2010 (now U.S. Pat. No. 8,163,764), which is a continuation-in-part of U.S. application Ser. No. 11/848,272, filed on Aug. 31, 2007, which is a continuation-in-part of: (i) U.S. application Ser. No. 11/499,936, filed on Aug. 7, 2006, which is a continuation-in-part of U.S. application Ser. No. 10/798,119, filed on Mar. 11, 2004, which is a continuation-in-part of U.S. application Ser. No. 10/205,738, filed on Jul. 25, 2002 (now U.S. Pat. No. 6,809,118); (ii) U.S. application Ser. No. 10/843,025, filed on May 10, 2004, which is a continuation-in-part of U.S. application Ser. No. 10/205,738, filed on Jul. 25, 2002 (now U.S. Pat. No. 6,809,118); and (iii) U.S. application Ser. No. 11/079,370, filed on Mar. 14, 2005, which is a continuation-in-part of U.S. application Ser. No. 10/132,999, filed on Apr. 26, 2002.

BACKGROUND

Skin is the largest organ of the human body. It has important functions in protecting the body from infection, toxins, microbes, and radiation. Disorders of skin not only compromise these functions, but also cause significantly psychological, social, and occupational problems. A significant portion of the world's population is afflicted with skin problems. Indeed, tens of millions of Americans are affected by of skin disorders such as rosacea, acne, pityriasis rosea, urticaria, and erythema. These disorders account for a large portion of annual healthcare costs, in addition to non-financial costs, such as intractable itching, sleep deprivation, time spent in treatment, inconvenience, and associated social stigma. There is a need for treatment of skin disorders.

SUMMARY

This invention is based, at least in part, on unexpected findings that a composition containing a histone hyperacetylating agent can be use to treat various skin disorder.

Accordingly, one aspect of this invention features a method for treating a skin disorder. The method includes administering to a subject in need thereof a composition having an effective amount of a histone hyperacetylating agent or a pharmaceutically acceptable salt thereof, and a cosmetically or pharmaceutically acceptable carrier. The disorder is rosacea, pityriasis rosea, erythema, rhinophyma, or a rosacea-associated disorder (e.g., pimple, papule, pustule, and telangiectasia).

The histone hyperacetylating agent can be a histone deacetylase (HDAC) inhibitor. Examples of the HDAC inhibitor include, but not limited to, trichostatin A, trichostatin C, oxamflatin, trapoxin A, FR901228, apicidin, HC-Toxin, WF27082, chlamydocin, salicylihydroxamic acid, suberoylanilide hydroxamic acid, azelaic bishydroxamic acid, azelaic-1-hydroxamate-9-an-ilide, M-carboxycinnamic acid bishydroxamide, 6-(3-chlorophenylureido)carpoic hydroxamic acid, MW2796, MW2996, sodium butyrate, arginine butyrate, isovalerate, valerate, 4-phenylbutyrate, sodium phenylbutyrate, propionate, butyramide, isobutyramide, phenylacetate, 3-bromopropionate, valproic acid, valproate, tributyrin, MS-27-275, a 3'-amino derivative of MS-27-275, depudecin, and scriptaid. The histone hyper-acetylating agent can be present in an amount of from 0.00001% to 100%, e.g., 0001% to 10%, by weight of the composition.

In one embodiment, the above-mentioned composition is a topical composition and the administering step is conducted by applying the composition to a surface of skin in need thereof of the subject. The composition can be a cream, an ointment, a gel, a paste, a powder, an aqueous solution, a spray, a suspension, a dispersion, a salve, a lotion, a patch, a suppository, a liposome formation, a mouth wash, an enema, an injection solution, an eye drop, an ear drop, a drip infusion, a microcapsule, or a nanocapsule. The composition can further contain a penetration enhancing agent, or a pH adjusting agent to provide a formulation pH in the range of approximately 2.0 to 13.0. It can be used as an adjuvant treatment following laser surgery or laser dermabrasion treatment to enhance aged and injured skin rejuvenation.

The above described method can further include administering to the subject a second agent. This second agent can include a cytokine, a cytokine antagonist, an interleukin, an interleukin antagonist, a growth factor, an angiogenic agent, an anti-histamine, an anti-fibrogenic agent, a vasoactive agent, an antibody, a conjugated antibody, an adenosine receptor agonist, a peroxisome proliferating activator receptor (PPAR) agonist, an anticholinergics, a non-steroid anti-inflammation drug (NSAID), a steroid, an anti-oxidant agent, a vitamin, a leukotriene modifier, a mast cell inhibitor, an anti-IgE antibody, lidocaine, epinephrine, a selective serotonin reuptake inhibitor (SSRI), a 5-hydroxytryptamine (5-HT) receptor antagonist, an antibiotics, a calcineurin inhibitor, an amino acid, a matrix metalloproteinase (MMP) inhibitor, a DNA methylation inhibitor, collagenase, clostridium histolyticum, or combinations thereof. The above-described composition and the second agent can be systemically or topically administered simultaneously or sequentially.

The above described method can further include identifying a subject having rosacea, pityriasis rosea, erythema, or rhinophyma before administering the composition or examining the subject for the therapeutic effect of the composition after administering the composition.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
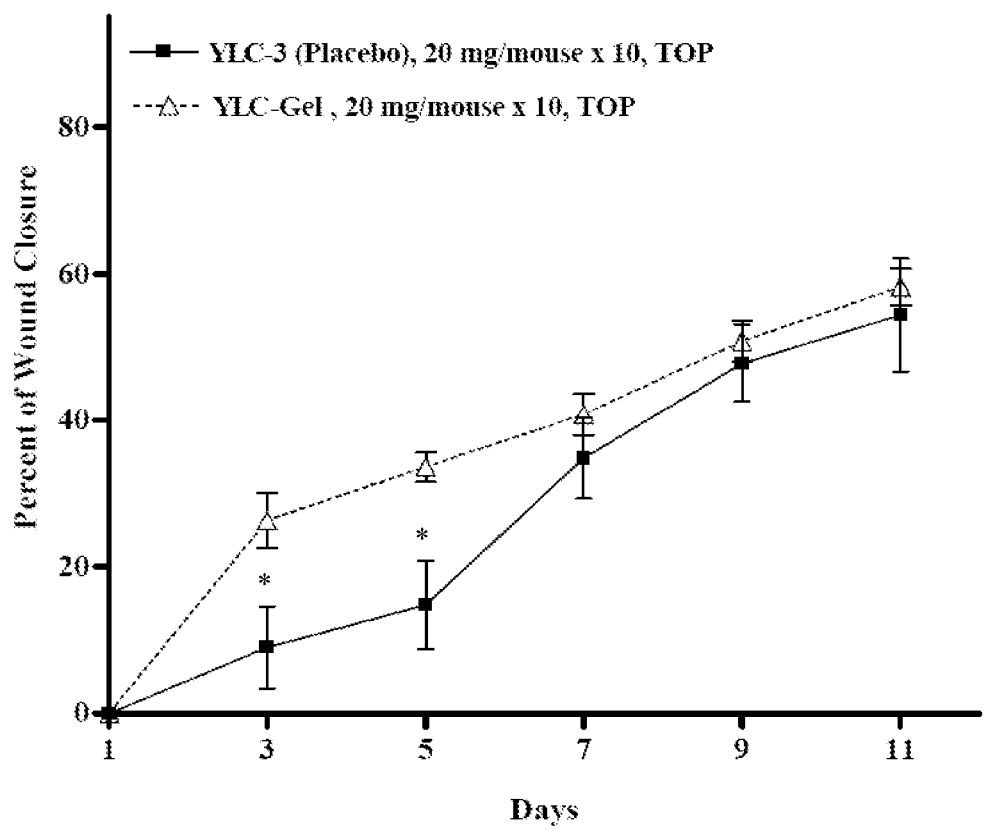
FIG. 1 is a diagram showing skin recovery and accelerated effect of a 5% sodium 4-phenylbutyrate (an HDAC inhibitor) gel (YLC-Gel) on skin regeneration after abrasive damage in a mouse model.

This invention is based, at least in part, on unexpected findings that a composition containing a histone hyperacetylating agent regulates and improves skin conditions. The present invention therefore features a method of using a histone hyperacetylating agent, e.g., a HDAC inhibitor, for treating skin disorders, such as rosacea, pityriasis rosea, erythema, and rhinophyma.

Rosacea is a chronic condition characterized by facial erythema or redness. Pimples are sometimes included as part of the definition. It primarily affects Caucasians of mainly northwestern European descent, but can also affect people of other ethnicities. Rosacea affects both sexes, but is almost three times more common in women. It has a peak age of onset between 30 and 60. Rosacea typically begins as redness on the central face across the cheeks, nose, or forehead, but can also less commonly affect the neck, chest, ears, and scalp. In some cases, additional symptoms, such as semi-permanent redness, telangiectasia (dilation of superficial blood vessels on the face), red domed papules (small bumps) and pustules, red gritty eyes, burning and stinging sensations, and in some advanced cases, a red lobulated nose (rhinophyma), may develop.

Pityriasis rosea is an acute, benign, self-limiting skin rash. It generally begins with a single "herald patch" lesion, followed in 1 or 2 weeks by a generalized body rash lasting about 6 weeks. It occurs most commonly in people between the ages of 10 and 35, but may occur at any age. The rash can last from several weeks to several months. Usually there are no permanent marks as a result of this condition, although some darker-skinned persons may develop long-lasting flat brown spots that eventually fade. It may occur at anytime of year, but pityriasis rosea is most common in the spring and fall. The cause of pityriasis rosea is unknown. It is not a sign of any internal disease, nor is it caused by a fungus, a bacteria, or an allergy. Recent evidence suggests that it may be caused by a virus since the rash resembles certain viral illnesses, and occasionally a person feels slightly ill for a short while just before the rash appears. Pityriasis rosea does not seem to spread from person to person and it usually occurs only once in a lifetime.

Erythema is a skin condition characterized by redness or rash. There are many types of erythema, including photosensitivity, erythema multiforme, and erythema nodosum. Photosensitivity is caused by a reaction to sunlight and tends to occur when something, such as an infection or a medication, increases your sensitivity to ultraviolet radiation. Erythema multiforme is characterized by raised spots or other lesions on the skin. It is usually caused by a reaction to medications, infections, or illness. Erythema nodosum is a form of erythema that is accompanied by tender lumps, usually on the legs below the knees, and may be caused by certain medications or diseases.

Rhinophyma is a slowly progressive condition due to hypertrophy of the sebaceous glands in the tip of nose; it is not a neoplasm. It presents as a pink, lobulated mass over the nose with superficial vascular dilation; and mostly affects men past middle age.

HDACs refer to enzymes that catalyze the removal of acetyl groups from lysine residues in the amino terminal tails of the nucleosomal core histones. As such, HDACs together with histone acetyl transferases (HATs) regulate the acetylation status of histones. Histone acetylation affects gene expression and inhibitors of HDACs, such as the hydroxamic acid-based hybrid polar compound suberoylanilide hydroxamic acid (SAHA), induce growth arrest, differentiation, and/or apoptosis of transformed cells in vitro and inhibit tumor growth in vivo. HDACs can be divided into three classes based on structural homology. Class I HDACs (HDACs 1, 2, 3 and 8) bear similarity to the yeast RPD3 protein, are located in the nucleus and are found in complexes associated with transcriptional co-repressors. Class II HDACs (HDACs 4, 5, 6, 7 and 9) are similar to the yeast HDA1 protein, and have both nuclear and cytoplasmic subcellular localization. Both Class I and II HDACs are inhibited by hydroxamic acid-based HDAC inhibitors, such as SAHA. Class III HDACs form a structurally distant class of nicotinamide (NAD) dependent enzymes that are related to the yeast SIR2 proteins and are not inhibited by hydroxamic acid-based HDAC inhibitors.

HDAC inhibitors, as used herein, refer to compounds that are capable of inhibiting the deacetylation of histones in vivo, in vitro, or both. As such, HDAC inhibitors inhibit the activity of at least one histone deacetylase. As a result of inhibiting the deacetylation of at least one histone, an increase in acetylated histone occurs and accumulation of acetylated histone is a suitable biological marker for assessing the activity of HDAC inhibitors. Therefore, procedures which can assay for the accumulation of acetylated histones can be used to determine the HDAC inhibitory activity of compounds of interest. It is understood that compounds which can inhibit histone deacetylase activity can also bind to other targets and as such can inhibit other biologically active molecules such as enzymes or non-histone proteins such as transcriptional factors, heat-shock proteins, chaperones and structural proteins.

HDAC inhibitors as a class of compounds with abilities in multiple gene regulation can modulate the expression of a specific set of genes by increasing histone acetylation, thereby regulating chromatin structure and accessibility of target genes for transcription and thus treating diseases (Marks, P A., et al., J. Natl. Cancer Inst., 92: 1210-6, 2000). HDAC inhibitors act selectively on gene expression, altering the expression of only about 2% of the genes expressed in cultured tumor cells. By modulating specific genes related to cell cycle control, DNA repair, tumor suppression, apoptosis and oncogenesis, HDAC inhibitors have shown to be potent inducers of growth arrest, differentiation, and/or apoptotic cell death of transformed cells in vitro and in vivo. Although the effects of HDAC inhibitors induce bulk histone acetylation, they result in apoptotic cell death, terminal differentiation, and growth arrest only in tumor cells but no toxicity in normal cells (Richon, V M., et al., Proc. Natl. Acad. Sci. USA., 97: 10014-10019, 2000; Van Lint, C., et al., Gene Expr., 5: 245-243, 1996). The epigenetic modification of chromatin structure for gene regulation suggests that HDAC inhibitors could be therapeutic candidates not only for cancers but also for genetic disorders such as cystic fibrosis, sickle cell anemia, beta-thalassemia, X-linked adrenoleukodystrophy, spinal muscular atrophy, and neurodegenerative disorders, and aging (Kemp S, et al. Nat Med 4: 1261-8, 1998; et al. Proc Natl Acad Sci USA 102: 11023-8, 2005; Kang H L, et al. Proc Natl Acad Sci USA 99: 838-43, 2002). On the other hand, HDAC inhibitors can also induce non-histone protein hyperacetylation. The hyperacetylation of nonhistone proteins such as ribosomal S3 or the Rel-A subunit of NF-kappaB will inhibit the NF-kappaB activity and suppress the pro-inflammatory cytokine production (Chen, L., et al., Science, 293: 1653-1657, 2001; Blanchard F, et al. Drug Discov Today 10: 197-204, 2005). Thus, in addition to the anti-cancer and gene modulation effects, HDAC inhibitors have also demonstrated anti-inflammatory effects on many inflammation diseases such as ulcerative colitis and autoimmune diseases (Segain, J P., et al., Gut, 47: 397403, 2000; Mishra, N., et al., Proc. Natl. Acad. Sci. USA., 98: 2628-2633, 2001; Leoni, F., et al., Proc. Natl. Acad. Sci. USA, 99: 2995-3000, 2002; Chung, Y L., et al., Mol. Ther. 8: 707-717, 2003).

On the basis of the abilities in coordinately, selectively, differentially and epigenetically modulating the expression of cell growth control genes, proinflammatory cytokines (IL-1, TNF-alpha), and fibrogenic growth factors (TGF-beta), a pharmaceutical composition comprising the HDAC inhibitor may provide an effective treatment not only to accelerate wound healing, to prevent scar formation, but also to treat skin disorders.

Active compounds used to carry out the present invention are, in general, hyperacetylating agents, such as HDAC inhibitors. Numerous such compounds are known. See, e.g., P. Dulski, Histone Deacetylase as Target for Antiprotozoal Agents, PCT Application WO 97/11366 (Mar. 27, 1997). Examples of such compounds include:

(i). trichostatin A and trichostatin C (Koghe et al. 1998. Biochem. Pharmacol. 56:1359-1364) (Trichostatin B has been isolated but not shown to be an HDAC inhibitor).

(ii). peptides, such as oxamflatin [(2E)-5-[3-[(phenylsufonyl) amino phenyl]-pent-2-en-4-ynohydroxamic acid (Kim et al. Oncogene, 18: 2461-2470 (1999)); trapoxin A (TPX)-cyclic tetrapeptide (cyclo-(L-phenylalanyl-L-phenylalanyl-D-pipecolinyl-L-2-amino-8-oxo-9,10-epoxy-decanoyl)) (Kijima et al., J. Biol. Chem. 268, 22429-22435 (1993)); FR901228 (Nakajima et al., Ex. Cell Res. 241, 126-133 (1998)); FR225497, cyclic tetrapeptide (H. Mori et al., PCT Application WO 00/08048 (Feb. 17, 2000)); apicidin [cyclo (N—O-methyl-L-tryptophanyl-L-isoleucinyl-D-pipecolinyl-L-2-amino-8-oxodecanoyl)-] (Darkin-Rattray et al., Proc. Natl. Acad. Sci. USA 93, 13143-13147 (1996)); apicidin 1a, apicidin Ib, apicidin Ic, apicidin IIa, and apicidin IIb (P. Dulski et al., PCT Application WO 97/11366); HC-Toxin, cyclic tetrapeptide (Bosch et al., Plant Cell 7, 1941-1950 (1995)); WF27082 (PCT Application WO 98/48825); and chlamydocin (Bosch et al., supra).

(iii). hydroxamic acid-based hybrid polar compounds (HPCs), such as salicylihydroxamic acid (SBHA) (Andrews et al., International J. Parasitology 30, 761-768 (2000)); suberoylanilide hydroxamic acid (SAHA) (Richon et al., Proc. Natl. Acad. Sci. USA 95, 3003-3007 (1998)); azelaic bishydroxamic acid (ABHA) (Andrews et al., supra); azelaic-1-hydroxamate-9-anilide (AAHA) (Qiu et al., Mol. Biol. Cell 11, 2069-2083 (2000)); M-carboxycinnamic acid bishydroxamide (CBHA) (Ricon et al., supra); 6-(3-chlorophenylureido) carpoic hydroxamic acid (3-Cl-UCHA) (Richon et al., supra); MW2796 (Andrews et al., supra); and MW2996 (Andrews et al., supra).

(iv). short chain fatty acid (SCFA) compounds, such as sodium butyrate (Cousens et al., J. Biol. Chem. 254, 1716-1723 (1979)); isovalerate (McBain et al., Biochem. Pharm. 53:1357-1368 (1997)); valproic acid and valerate (McBain et al., supra); 4-phenylbutyrate (4-PBA) (Lea and Tulsyan, Anti-cancer Research, 15, 879-873 (1995)); phenylbutyrate (PB) (Wang et al., Cancer Research, 59, 2766-2799 (1999)); propionate (McBain et al., supra); butyramide (Lea and Tulsyan, supra); isobutyramide (Lea and Tulsyan, supra); phenylacetate (Lea and Tulsyan, supra); 3-bromopropionate (Lea and Tulsyan, supra); and tributyrin (Guan et al., Cancer Research, 60, 749-755 (2000)).

(v). benzamide derivatives, such as MS-27-275 [N-(2-aminophenyl)-4-[N-(pyridin-3-yl-methoxycarbonyl)aminomethyl]benzamide] (Saito et al., Proc. Natl. Acad. Sci. USA 96, 4592-4597 (1999)); and 3'-amino derivative of MS-27-275 (Saito et al., supra).

(vi). other inhibitors, such as depudecin (Kwon et al. 1998. PNAS 95:3356-3361); and scriptaid (Su et al. 2000 Cancer Research, 60:3137-3142).

The compositions can further include a second active compound. Examples of such a second compound include, but are not limited to, a cytokine, a cytokine antagonist, an interleukin, an interleukin antagonist, a growth factor, an angiogenic agent, an anti-histamine, an anti-fibrogenic agent, a vasoactive agent, an antibody, a conjugated antibody, an adenosine receptor agonist, a peroxisome proliferating activator receptor (PPAR) agonist, an anticholinergics, a non-steroid anti-inflammation drug (NSAID), a steroid, an anti-oxidant agent, a vitamin, a leukotriene modifier, a mast cell inhibitor, an anti-IgE antibody, lidocaine, epinephrine, a selective serotonin reuptake inhibitor (SSRI), a 5-hydroxytryptamine (5-HT) receptor antagonist, an antibiotics, a calcineurin inhibitor, an amino acid, a matrix metalloproteinase (MMP) inhibitor, a DNA methylation inhibitor collagenase, and clostridium histolyticum.

The compounds described above can be formulated as pharmaceutical or cosmetic compositions.

A pharmaceutical composition of this invention can contain a pharmaceutically acceptable carrier, such as a solvent, a dispersion medium, a coating, an antibacterial and antifungal agent, and an isotonic and absorption delaying agent. A "pharmaceutically acceptable carrier," after administered to or upon a subject, does not cause undesirable physiological effects. The carrier in the pharmaceutical composition must be "acceptable" also in the sense that it is compatible with the active ingredient and, preferably, capable of stabilizing it. One or more solubilizing agents can be utilized as pharmaceutical carriers for delivery of an active compound. Examples of other carriers include colloidal silicon oxide, magnesium stearate, cellulose, sodium lauryl sulfate, and D&C Yellow #10. The composition can additionally include binding agents (e.g., pregelatinized maize starch, polyvinylpyrrolidone, or hydroxypropyl methylcellulose); binders or fillers (e.g., lactose, pentosan, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets or capsules can be coated by methods well known in the art.

Such compositions can be administered orally, parenterally, by inhalation spray, rectally, vaginally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Also within the scope of this invention is a cosmetic composition that contains one or more active compounds described above. This composition contains a safe and effective amount of a dermatologically acceptable carrier that is suitable for topical application to the skin.

A "cosmetically acceptable" or "dermatologically-acceptable" composition or component refers a composition or component that is suitable for use in contact with human skin without undue toxicity, incompatibility, instability, allergic response, and the like. It enables an active compound and optional component to be delivered to the skin at an appropriate concentration(s). The carrier can thus act as a diluent, dispersant, solvent, or the like to ensure that the active materials are applied to and distributed evenly over the selected target at an appropriate concentration. The carrier can be solid, semi-solid, or liquid. Preferably, it is in the form of a lotion, a cream, or a gel, in particular one that has a sufficient thickness or yield point to prevent the active materials from sedimenting. The carrier can be inert or possess dermatological benefits of its own. It should also be physically and chemically compatible with the active components described herein, and should not unduly impair stability, efficacy, or other use benefits associated with the composition.

A safe and effective amount refers to an amount of a compound, component, or composition sufficient to significantly induce a positive benefit, preferably a positive skin appearance or feel benefit, including independently the benefits disclosed herein, but low enough to avoid serious side effects, i.e., to provide a reasonable benefit to risk ratio, within the scope of sound medical judgment.

The type of carrier utilized in the cosmetic composition depends on the type of product form of the composition. A cosmetic composition may be made into a wide variety of product forms such as those known in the art. These include, but are not limited to, lotions, creams, gels, sticks, sprays, ointments, pastes, and mousses. These product forms may comprise several types of carriers including, but not limited to, solutions, aerosols, emulsions, gels, solids, and liposomes.

The compositions or preparations for treating a skin disorder or improvement of skin conditions are generally aimed at providing a condition for increasing skin manageability. There are recognized categories of formulations for skin care compositions, including creams, ointments, gels, sprays, lotions, skin tonics, shampoos or mousses as referred to above. Skin sprays are generally composed of aerosolized copolymers, such as polyvinylpyrrolidone, vinyl acetate and the like, and may also function as a setting lotion. Skin gel preparations are similar to sprays in composition, but are in gel and alcohol free form, and can coat the skin. Skin mousse is foam released under pressure from an aerosolized can. The short-chain fatty acid derivative active ingredient in a topical skin care composition according to the present invention is preferably present at a concentration of 0.00001 to 100.00% by weight relative to the total weight of the composition, or in a dosage of 1 to 1000 mg. A skin care composition for rejuvenating skin according to the present invention may be formulated as a hydrophobic or hydrophilic cream, ointment, gel, emollient, spray, lotion, skin tonic, shampoo, body wash or mousse as referred to above, suitably with additional ingredients suitable for use in skin care compositions of types known in the art, and such further ingredients can include petrolatum, waxes, lanolin, silicone, liposomes, vegetable, mineral oils, plasticizers, fragrances, preservatives, a penetration enhancing agent, a pH adjusting agent or other suitable ingredients for topical skin compositions. Such ingredients can moisturize skin, stabilize the active compound, increase drug-skin contact and local concentration, control drug slow release, and/or aid in decreasing skin erythema and breakage, preventing skin atrophy, fibrosis and infection, and promoting skin wound healing.

Pharmaceutically acceptable salts for the components to be employed according to the present subject matter are those with inorganic cations, for example alkali metal salts, in particular sodium, potassium, or ammonium salts, alkaline earth metal salts such as, in particular, the magnesium or calcium salts, as well as salts with bi- or tetravalent cations, for example the zinc, aluminum, or zirconium salts. Also contemplated are salts with organic bases, such as dicyclohexylamine salts; methyl-D-glucamine; and salts with amino acids, such as arginine, lysine, histidine, glutamine and so forth. Also, the basic nitrogen-containing groups can be quaternized with such agents as: lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; asthma halides, such as benzyl and phenethyl bromides; and others. Salt-forming agents, for example, low molecular weight alkylamines such as methylamine, ethylamine, or triethylamine can also be employed. Water or oil-soluble or dispersible products are thereby obtained.

The amount of active ingredient that can be combined with the carrier materials to produce a single dosage form will vary depending upon the subject and the particular mode of administration. The dosage required will vary according to a number of factors known to those skilled in the art, including, but not limited to, the compound or compounds used, the species of subject, the size of the subject, and the severity of the signs and symptoms of the skin. The compounds can be administered in a single dose, in multiple doses throughout a 24-hour period, or by continuous infusion. When administered by continuous infusion, the compounds can be supplied by methods well known in the art, such as, but not limited to, intravenous gravity drip, intravenous infusion pump, implantable infusion pump, or any topical routes. Treatment of the subject with an HDAC inhibitor alone or in combination with other agents of the invention may last for the life of the subject.

The above-described compositions can contain one or more prodrugs. The "pro-drugs" refers to therapeutic agents or compounds that undergo biotransformation prior to exhibiting their pharmacological effects. The chemical modification of drugs to overcome pharmaceutical problems has also been termed "drug latentiation." Drug latentiation is the chemical modification of a biologically active compound to form a new compound which upon in vivo enzymatic attack will liberate the parent compound. The chemical alterations of the parent compound are such that the change in physiochemical properties will affect the drug's absorption, distribution and enzymatic metabolism. The definition of drug latentiation has also been extended to include nonenzymatic regeneration of the parent compound. Regeneration takes place as a consequence of hydrolytic, dissociative, and other reactions not necessarily enzyme mediated. The terms pro-drugs, latentiated drugs, and bioreversible derivatives are used interchangeably. By inference, latentiation implies a time lag element or time component involved in regenerating the bioactive parent molecule in vivo. The term pro-drug is general in that it includes latentiated drug derivatives as well as those substances which are converted after administration to the actual substance which combines with receptors. The term pro-drug is also a generic term for agents which undergo biotransformation prior to exhibiting their pharmacological actions. In the case where the administered drug is not the active agent, but rather is biotransformed to the active agent, the term "HDAC inhibitor" as "pro-drug" also includes compounds which may not necessarily undergo biotransformation to the administered drug but may undergo biotransformation to the active agent which exhibits the desired pharmacological effect.

The above-described compositions are particularly useful for improving aesthetic appearance of skin and for producing smooth skin. Accordingly, this invention features a method of treating a number of skin disorders. Examples of these disorders include rosacea, acne, pityriasis rosea, inflammatory skin reactions such as urticaria (swelling with raised edges), general swelling, and erythema. The method includes administering to a subject in need thereof a composition containing an effective amount of the above-described histone hyperacetylating agent or a pharmaceutically acceptable salt thereof, and a cosmetically or pharmaceutically acceptable carrier. In one embodiment, the method is used to treat one or more of the disorders, where no or little itchiness is involved.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds. In a preferred embodiment, the subject is a human. In another embodiment, the subject is an experimental animal or animal suitable as a disease model. A subject to be treated for the above-described disorder can be identified by standard diagnosing techniques for the disorder.

"Treating" refers to administration of a compound to a subject, which has one of the above-mentioned disorders, with the purpose to cure, alleviate, relieve, remedy, delay the onset of, or ameliorate the disorder, the symptom of the disorder, the disease state secondary to the disorder, or the predisposition toward the disorder. An "effective amount" refers to an amount of the compound that is capable of producing a medically desirable result, e.g., as described above, in a treated subject. The treatment method can be performed alone or in conjunction with other drugs or therapy.

The present invention also aims at providing methods and compositions having one HDAC inhibitor or at least one HDAC inhibitor in combination with other compounds for treating skin disorders.

Regulating skin conditions can be carried out prophylactically or therapeutically. Prophylactical regulation includes delaying, minimizing, or preventing the above-mentioned disorders. Therapeutic regulation, on the other hand, includes treating the above-mentioned disorders or ameliorating, diminishing, minimizing or effacing symptoms of these disorders. Regulating skin conditions involves improving skin appearance feel, e.g., providing a smoother and more even appearance.

To use a topical composition of this invention, one can topically apply to the skin a safe and effective amount of the composition. The applied amount, the frequency of application and the period of use vary widely depending upon the active levels of a given composition and the level of treatment or regulation desired, e.g., in light of the level of skin disorder or ageing present in the subject and the rate of further skin ageing.

A wide range of quantities of the compositions of the present invention can be employed to provide a skin appearance and/or feel benefit. Quantities of the compositions typically applied per application are from about 0.1 mg/cm$^2$ to about 10 mg/cm$^2$, e.g., 2 mg/cm$^2$. Typically, a composition can be used once per day. However, application rates can vary from about once per week up to about three times per day or more.

The topical composition of this invention provides a visible improvement in skin condition essentially immediately following application of the composition to the skin. Such immediate improvement involves coverage or masking of skin imperfections such as textural discontinuities or providing a more even skin tone or color. The compositions of the invention also provide visible improvements in skin condition following chronic topical application. "Chronic topical application" involves continued topical application of a composition over an extended period during the subject's lifetime, preferably for a period of at least about one week, one month, three months, six months, or one year. Chronic regulation of skin condition involves improvement of skin condition following multiple topical applications.

Regulating skin conditions is preferably performed by applying a composition in the form of a skin lotion, cream, cosmetic, or the like which is intended to be left on the skin for an extended period for some aesthetic, prophylactic, therapeutic or other benefit (i.e., a "leave-on" composition). As used herein, "leave-on" compositions exclude rinse-off skin cleansing products. After applying the composition to the skin, the leave-on composition is preferably left on the skin for a period of at least about 15 minutes, 30 minutes, 1 hour, or up to about 12 hours.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein, including the prior applications, are hereby incorporated by reference in their entirety. Further, any mechanism proposed below does not in any way restrict the scope of the claimed invention.

Example 1

Preparation of an Oleaginous Ointment of Phenylbutyrate

Sixty-five gram (65 g) of white petrolatum (Riedel-de Haen), 15 g of cetyl alcohol (Riedel-de Haen), 260 g of soft paraffin (Merck), 155 g of liquid paraffin (Merck), and 5 g of 4-phenylbutyrate (Merck) were mixed in a beaker and heated at 70° C. to form a paste. The paste was stirred at 400 rpm for 1 hour, and then cooled at room temperature.

Preparation of a Cream of Phenylbutyrate

Part I: 70 g of Tefose 63™, 20 g of Superpolystate™, 10 g of Coster 5000™, 15 g of Myriyol 318™, 15 g of Coster 5088™, and 15 g of GMS SE™ (all commercially available from a local supplier) were mixed in a beaker and heated at 70° C.

Part II: 5.739 g of sodium 4-phenylbutyrate (Triple Crown America, Inc.), 0.125 g of methylparaben (Merck), 0.075 g of propylparaben (Merck), and 149.061 g of deionized water were mixed in a beaker and heated at 70° C.

Part II was slowly added into part I and continually stirred at 400 rpm for 5 minutes to form a mixture. 2% Stabileze QM™ (prepared by dissolving 2 g of Stabileze QM™ in 98 g of deionized water, heating and stirring at 70° C. to form a paste, and cooling at room temperature) was added into the mixture and stirred for 5 minutes. The pH of the mixture was adjusted to 5.34 with 0.85% phosphoric acid (Merck), and stirred at 600 rpm for 20 minutes. The mixture was cooled at room temperature.

Preparation of a Gel of Phenylbutyrate

Part I: 10 g of Stabileze QM™ and 232.035 g of deionized water were mixed in a beaker and heated at 70° C.

Part II: 5.739 g of sodium 4-phenylbutyrate (Triple Crown America, Inc.), 0.125 g of methylparaben (Merck), 0.075 g of propylparaben (Merck), 232.035 g of deionized water, and 20 g of 10% NaOH were mixed in a beaker and heated at 70° C.

Part II was slowly added into Part I and continually stirred at 400 rpm for 20 minutes to form a mixture. The mixture was cooled at room temperature.

Preparation of a Liposomal Formulation of Phenylbutyrate

In this liposomal formulation, egg phosphatidylcholine (EPC) and cholesterol were used in equi- or different-molar concentrations as primary lipid components. Various liposomes located with 4-phenylbutyrate were obtained by varying the lipid:phenylbutyrate ratio. Liposomes were prepared by thin film hydration, sized by membrane extrusion, and physically evaluated.

Preparation of Ointment of Trichostatin A

To prepare the ointment, 472.5 g of white petrolatum (Riedel-de Haen), 27 g of paraffin wax 50/52 (local supplier), and 0.5 g of trichostatin A (sigma) were mixed in a beaker and heated at 70° C. to form a paste. The paste was stirred at 400 rpm for 1 hour, and then cooled at room temperature.

Preparation of an Oleaginous Ointment of Trichostatin A

To prepare the ointment, 67.5 g of white petrolatum (Riedel-de Haen), 16 g of cetyl alcohol (Riedel-de Haen), 260.5 g of soft paraffin (Merck), 155.5 g of liquid paraffin (Merck), and 0.5 g of trichostatin A (sigma) were mixed in a beaker and heated at 70° to form a paste. The paste was stirred at 400 rpm for 1 hour, and then cooled at room temperature.

Preparation of Cream of Valproic Acid

Part I: 70 g of Tefose 63®, 20 g of Superpolystate®, 10 g of Coster 5000®, 15 g of Myriyol 318®, 15 g of Coster 5088®, and 15 g of GMS SE.® (all commercially available from local supplier) were mixed in a beaker and heated at 70° C.

Part II: 5.739 g of valproic acid (sigma), 0.125 g of methylparaben (Merck), 0.075 g of propylparaben (Merck), and 149.061 g of deionized water were mixed in a beaker and heated at 70° C.

Part II was slowly added into Part I and continually stirred at 400 rpm for 5 minutes to form a mixture. 2% Stabileze QM®.D (prepared by dissolving 2 g of Stabileze QM® in 98 g of deionized water, heating and stirring at 70° C. to form a paste, and cooling at room temperature) was added into the mixture and stirred for 5 minutes. The pH of the mixture was adjusted to 5.34 with 0.85% phosphoric acid (Merck), and stirred at 600 rpm for 20 minutes. The mixture was cooled at room temperature.

Example 2

In this example, assays were conducted to show that an HDAC inhibitor was effective for skin regeneration after abrasive skin damage.

Groups of 5 ICR derived male mice weighing 22±2 g, provided by animal breeding center of MDS Pharma Service-Taiwan, Ltd., were used. Under hexobarbital (90 mg/kg, IP) anesthesia, the shoulder and back region of each animal was shaved. A sharp punch (ID 12 mm) was used to remove the skin including panniculus carnosus and adherent tissues. The wound area, traced onto the clear plastic sheets on day 3, 5, 7, 9, and 11, were quantified by use of an Image Analyzer (Life Science Resources VISTA, Ver. 3.0). The formulation of 5% sodium 4-phenylbutyrate gel or placebo at a dose of 200 µg/mouse was applied topically immediately following injury and once daily thereafter for a total of 10 consecutive days. The wounds half-closure time (CT50) was determined by linear regression using Graph-Pad Prism (Graph Pad Software USA) and unpaired Student's t test was applied for comparison between the phenylbutyrate treated and placebo group at each measurement time point. Differences were considered statistically significant at $p<0.05$ (*). As shown in FIG. 1, the phenylbutyrate gel significantly promoted skin regeneration since Day 3 ($p<0.05$).

Example 3

In this example, assays were conducted to show that an HDAC inhibitor produced smoother skin after skin recovery from radiation damage.

Adult female Sprague Dawley (SD) rats were purchased from the animal center of the National Science Council of Taiwan, and weighed 250-300 g at the time of irradiation. Each rat was caged alone and allowed chow and water. They were anesthetized with pentobarbital 50 mg/kg i.p. before irradiation. The skin over the gluteal area was shaved completely and radiation fields with 2-cm diameter were outlined with a marking pen just prior to irradiation. An electron beam with 6 MeV energy produced by a linear accelerator was used. The dose was delivered on Day 0 at 4 Gy/min up to 40 Gy to the prepared area. One group with skin irradiation was treated by vehicle, another group with skin irradiation was treated by a 5% phenylbutyrate gel, and the third group with skin irradiation was left untreated. The vehicle and phenylbutyrate gel were applied topically to the irradiated skin twice daily from Day 1 to Day 90 after irradiation. The mean dosage for each treatment in the respective groups was 50 mg phenylbutyrate per $cm^2$ skin, and an equivalent amount of the vehicle base for the control groups. The irradiated skins were subjected to H&E histology.

The group treated with phenylbutyrate for 180 days had smooth skin, thicker epidermis with more cell layers but have thinner dermis (measured from epidermis to the subcutaneous fat layer) with less fragmented collagen deposition when compared to the control groups (normal skin and acute reaction on Day 7). In contrast, the vehicle group showed obvious skin wrinkles with more fragmented collagen deposit.

Example 4

Immunofluorescence was conducted to show that an HDAC inhibitor suppressed TGF-beta, a Fibrogenic Growth Factor, in the late skin remodeling to prevent skin deformation.

The same pathological sections described in Example 3 were subjected to immunofluorescence with the anti-TGF-beta 1 and 2 antibodies. The TGF-beta protein, a strong fibrogenic factor, was up-regulated by irradiation, and highly expressed in fibrogenic skin both in keratinocytes of the epidermis and in myofibroblasts of the dermis on Day 7 and Day 180 in the acute reaction and vehicle-treated group, respectively. However, the expression of TGF-beta was suppressed effectively in the phenylbutyrate-treated group on Day 180 which showed less fragmented collagen deposit compared to the control groups.

Example 5

Immunohistochemistry was conducted to show that TNF-alpha, a proinflammatory cytokine, was suppressed by an HDAC inhibitor in the late skin remodeling to prevent chronic skin ulceration.

On Day 270, three of five rats in Vaseline-treated group and four of five rats in the vehicle-treated group, compared with zero of five rats in the phenylbutyrate-treated group, showed chronic ulceration, necrosis, bullae formation, and inflammatory cell infiltration. The decrease in late radiation-induced skin damage by topical phenylbutyrate was consistent with the suppression of TNF-alpha expression.

Example 6

In this example, assays were conducted to show that an HDAC inhibitor promoted the skin rejuvenation from infection, inflammation, and immune reaction.

Groups of 5 Long Evans rats weighing 150±20 g were used. A well-ground suspension of killed Mycobacterium tuberculosis (DIFCO, USA; 0.3 mg in 0.1 ml of light mineral oil; Complete Freund's Adjuvant, CFA) was administered into the subplantar region of the right hind paw. The skin wound was induced by the Mycobacterium tuberculosis injection into the sub-plantar region. The 10% of phenylbutyrate ointment at a dose of 200 mg/paw was applied topically twice daily for 18 consecutive days after bacterial injection.

Skin rejuvenation is promoted in the plantar skin wound in the treated group using phenylbutyrate.

Example 7

In this example, assays were conducted to show that an HDAC inhibitor led to improvement of aesthetic appearance of skin. A 60-year-old female with rosacea-associated erythema and papules of the nose and cheeks initially applied the 2.5% sodium 4-phenylbutyrate gel to her face 2-3 times a day. By the third day improvement was evident. Then application of the topical gel decreased in frequency to once a day or few times a week. After several months her face was completely clear of rosacea-associated redness and papules.

The gel was also used on three other persons who had rosacea (one male and two female) in the same manner. After the treatment, it was found that their faces were also free of rosacea-associated redness and papules.

Example 8

In this example, assays were conducted to show that an HDAC inhibitor ameliorated the tyrosine kinase inhibitor (TKI)-augmented skin reaction in a mouse model.

Tyrosine kinase inhibitors (TKIs) cause acneform-like skin toxicities in humans. To induce the TKI-augmented skin reaction in a mouse model, groups (n=5, each) of BALB/c male mice weighing 22±2 g received topical application on the ear skin with 10 μL of the solutions of a TKI (PD168393) (4 mmol/L) dissolved in DMSO/absolute ethanol (1/10) 30 minutes before 10 μL of 0.5% 2,4-dinitrofluorobenzene (DNFB) irritation on the ear of testing animals (Pastore S, et al. J Immunol 174:5047-5056, 2005).

To test the therapeutic drug effects on the TKI-augmented skin reaction, a 2.5% sodium 4-phenylbutyrate gel or placebo (gel base) was applied topically on the right ear 3 times at 3-hour interval before hand on day 0 and day 1. On day 1, 60 minutes after the first dosing of phenylbutyrate or placebo, the TKI (PD168393) was applied topically 30 minutes before 0.5% DNFB irritation on the right ear skin. The second and third dosing of phenylbutyrate and placebo on day 1 were applied 1 hour and 3 hours after DNFB irritation. Ear swelling was measured with a Dyer model micrometer gauge at 0, 3, 6, 8, 24 and 48 hours after DNFB irritation. As a treatment control for comparison, the strong steroid, dexamethasone (0.3 mg), was administered topically 60 minutes before and 15 minutes after DNFB irritation in a control group. The right and left ear thickness of each mouse was measured with a Dyer model micrometer gauge. Ear edema was calculated by subtracting the thickness of the left ear (normal control) from the right ear (treated ear).

Figure 2:
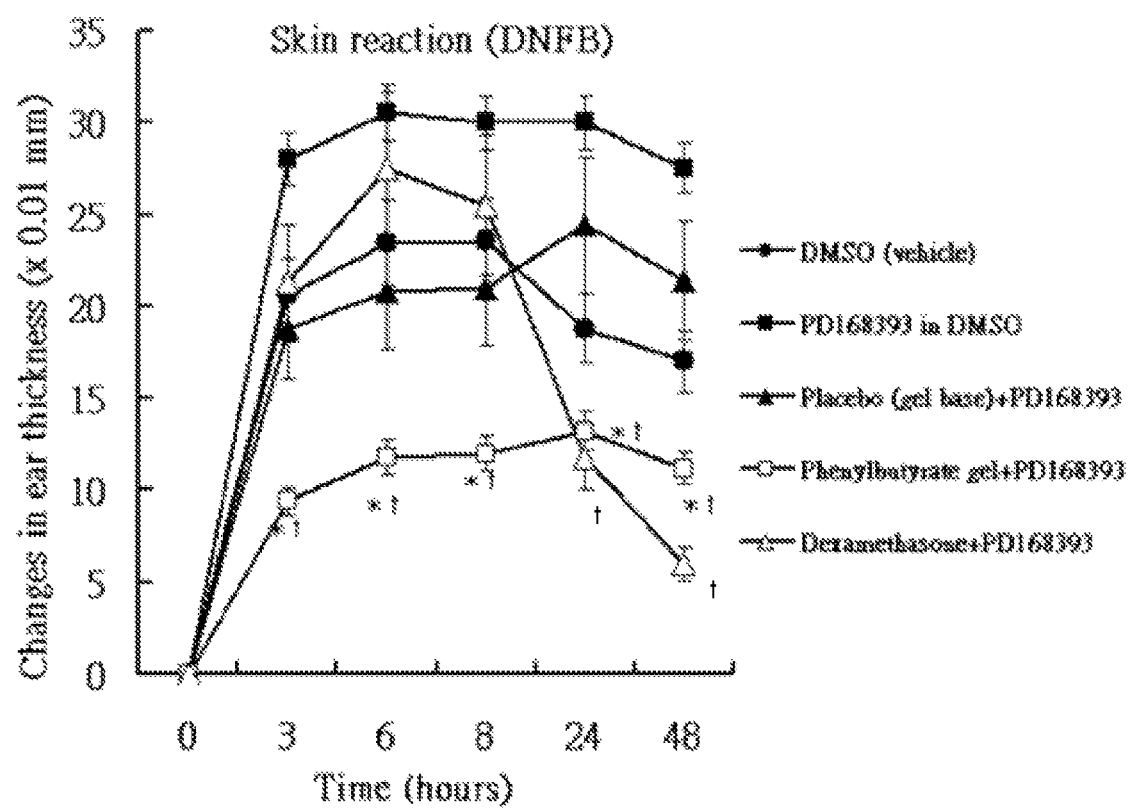
FIG. 2 are a time-course diagram showing that the topical 2.5% phenylbutyrate gel suppresses the tyrosine kinase inhibitor (PD168393)-induced skin reaction in a mouse model. PD168393 induces acneform-like skin lesions in humans, and augments skin swelling in mice after DNFB irritation.

Topical administration of 4 mM of the TKI (PD168393) alone, DMSO alone, the placebo gel base only, or the 2.5% phenylbutyrate gel alone had no effect on ear thickness, and did not induce any change in normal skin histology. By contrast, 4 mM of the TKI (PD168393) applied 30 minutes before DNFB irritation led to aggravation of the DNFB-induced skin response. However, the skin pre-treated with the 2.5% phenylbutyrate gel resulted in a significant reduction of the TKI-augmented ear swelling induced by DNFB irritation at 3, 6, 8, 24, and 48 hours after DNFB irritation as compared to the skin pre-treated with the placebo gel base (FIG. 2). Dexamethasone did not suppress the TKI-augmented skin reaction at 3, 6, and 8 hours after DNFB irritation. Therefore, these results suggest that the potent steroid, dexamethasone, is not effective on suppression of the TKI-augmented skin reaction, but the 2.5% phenylbutyrate gel appears to have therapeutic benefit on the dermatoloical side effects related to the tyrosine kinase inhibition which will induce acneform skin lesions in humans.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

A number of embodiments of the invention have been described. Nevertheless, it will be understood that various modifications may be made without departing from the spirit and scope of the invention. Accordingly, other embodiments are within the scope of the following claims.

What is claimed is:

1. A method for treating a skin disorder, comprising administering to a subject in need thereof a composition containing an effective amount of a histone hyperacetylating agent or a pharmaceutically acceptable salt thereof, and a cosmetically or pharmaceutically acceptable carrier, wherein the skin disorder is selected from the group consisting of rosacea, pityriasis rosea, erythema, rhinophyma, and a rosacea-associated disorder that is pimple, papule, pustule, or telangiectasia, and the histone hyperacetylating agent is selected from the group consisting of trichostatin A, trichostatin C, oxamflatin, trapoxin A, FR901228, apicidin, HC-Toxin, WF27082, chlamydocin, salicylihydroxamic acid, suberoylanilide hydroxamic acid, azelaic bishydroxamic acid, azelaic-1-hydroxamate-9-an-ilide, M-carboxycinnamic acid bishydroxamide, 6-(3-chlorophenylureido) carpoic hydroxamic acid, MW2796, MW2996, sodium butyrate, arginine butyrate, isovalerate, valerate, 4-phenylbutyrate, propionate, butyramide, isobutyramide, phenylacetate, 3-bromopropionate, valproic acid, valproate, tributyrin, MS-27-275 or a 3'-amino derivative thereof, depudecin, and scriptaid.

2. The method of claim 1, wherein the composition is a topical composition.

3. The method of claim 2, wherein the histone hyperacetylating agent is trichostatin A or trichostatin C.

4. The method of claim 2, wherein the histone hyperacetylating agent is oxamflatin, trapoxin A, FR901228, apicidin, HC-Toxin, WF27082, or chlamydocin.

5. The method of claim 2, wherein the histone hyperacetylating agent is salicylihydroxamic acid, suberoylanilide hydroxamic acid, or azelaic bishydroxamic acid.

6. The method of claim 2, wherein the histone hyperacetylating agent is azelaic-1-hydroxamate-9-an-ilide, M-carboxycinnamic acid bishydroxamide, 6-(3-chlorophenylureido) carpoic hydroxamic acid, MW2796, or MW2996.

7. The method of claim 2, wherein the histone hyperacetylating agent is sodium butyrate, arginine butyrate, isovalerate, valerate, 4-phenylbutyrate, propionate, butyramide, isobutyramide, phenylacetate, 3-bromopropionate, valproic acid, valproate, or tributyrin.

8. The method of claim 2, wherein the histone hyperacetylating agent is MS-27-275 or a 3'-amino derivative thereof.

9. The method of claim 2, wherein the histone hyperacetylating agent is depudecin or scriptaid.

10. The method of claim 2, wherein the composition is a cream, an ointment, a gel, a paste, a powder, an aqueous solution, a spray, a suspension, a dispersion, a salve, a lotion, a patch, a suppository, a liposome formulation, a mouth wash, an enema, an eye drop, an ear drop, a microcapsule formulation, or a nanocapsule formulation.

11. The method of claim 1, wherein the method further comprises administering to the subject a second agent that is a cytokine, a cytokine antagonist, an interleukin, an interleukin antagonist, a growth factor, an angiogenic agent, an antihistamine, an anti-fibrogenic agent, a vasoactive agent, an antibody, a conjugated antibody, an adenosine receptor agonist, a peroxisome proliferating activator receptor agonist, an anticholinergics, a non-steroid anti-inflammation drug, a steroid, an anti-oxidant agent, a vitamin, a leukotriene modifier, a mast cell inhibitor, an anti-IgE antibody, lidocaine, epinephrine, a selective serotonin reuptake inhibitor, a 5-hydroxytryptamine receptor antagonist, an antibiotics, a calcineurin inhibitor, an amino acid, a matrix metalloproteinase inhibitor, a DNA methylation inhibitor, collagenase, clostridium histolyticum, or combinations thereof.

12. The method of claim 11, wherein the composition and the second agent are topically administered simultaneously or separately.

13. The method of claim 1, wherein the skin disorder is rosacea.

14. The method of claim 13, wherein the composition is a topical composition.

15. The method of claim 14, wherein the histone hyperacetylating agent is sodium butyrate, arginine butyrate, isovalerate, valerate, 4-phenylbutyrate, propionate, butyramide, isobutyramide, phenylacetate, 3-bromopropionate, valproic acid, valproate, or tributyrin.

16. The method of claim 15, wherein the histone hyperacetylating agent is sodium 4-phenylbutyrate.

17. The method of claim 1, wherein the skin disorder is pityriasis rosea.

18. The method of claim 1, wherein the skin disorder is erythema.

19. The method of claim 1, wherein the skin disorder is rhinophyma.

* * * * *